United States Patent
Wang et al.

(10) Patent No.: US 7,018,333 B2
(45) Date of Patent: Mar. 28, 2006

(54) METHOD AND SYSTEM FOR INSTANT BIOPSY SPECIMEN ANALYSIS

(75) Inventors: Shih-Ping Wang, Los Altos, CA (US); Tommy Earl Cupples, Columbia, SC (US); Xiangyong Cheng, Cupertino, CA (US)

(73) Assignee: U-Systems, Inc., San Jose, CA (US)

( * ) Notice: Subject to any disclaimer, the term of this patent is extended or adjusted under 35 U.S.C. 154(b) by 137 days.

(21) Appl. No.: 10/466,568

(22) PCT Filed: Nov. 20, 2001

(86) PCT No.: PCT/US01/43244

§ 371 (c)(1), (2), (4) Date: Apr. 2, 2004

(87) PCT Pub. No.: WO02/41752

PCT Pub. Date: May 30, 2002

(65) Prior Publication Data

US 2004/0152981 A1 Aug. 5, 2004

Related U.S. Application Data

(60) Provisional application No. 60/252,942, filed on Nov. 24, 2000.

(51) Int. Cl.
*A61B 8/00* (2006.01)

(52) U.S. Cl. ....................................................... 600/443

(58) Field of Classification Search ......... 600/437–472
See application file for complete search history.

(56) References Cited

U.S. PATENT DOCUMENTS 5,398,690 A * 3/1995 Batten et al. ................ 600/461
2003/0065260 A1 * 4/2003 Cheng et al. ............... 600/427

OTHER PUBLICATIONS

"Automated Detection of Breast Tumors in Ultrasonic Images Using Fuzzy Reasoning" X. Y. Cheng, et al., Proceedings of the International Conference on Image Processing vol. III, IEEE Computer Society, Los Alamitos, CA 1997.
"A Study on Automated Extraction of Breast Tumors Using Three Dimensional Ultrasonic Echography" X. Y. Cheng, Keio University, Yokohama, Japan 1997.

* cited by examiner

*Primary Examiner*—Ali Imam
(74) *Attorney, Agent, or Firm*—Cooper & Dunham LLP

(57) ABSTRACT

An apparatus and related methods for ultrasound-assisted surgical removal of a tumor or other biological object from a patient, the tumor requiring complete removal such that no portion thereof remains inside the patient, is described. According to a preferred embodiment, a specimen containing the tumor is extracted from the patient and suspended in a container holding an acoustically conductive fluid. An ultrasound probe is brought into acoustic communication with the fluid and scans the specimen, preferably at an acoustic power setting higher than a maximum ultrasonic power permitted on live human tissue. Resulting two-dimensional and/or three-dimensional ultrasound images of the specimen, which have a higher quality due to the increased acoustic power of the scan, are viewed on an output display for examining whether any portion of the tumor comes into contact with a surface of the specimen. Preferably, the ultrasound images are segmented and processed by the ultrasound system in a manner that further assists in the determination of whether the specimen contains the entire tumor.

21 Claims, 3 Drawing Sheets

METHOD AND SYSTEM FOR INSTANT BIOPSY SPECIMEN ANALYSIS

CROSS-REFERENCE TO RELATED APPLICATIONS

This application is the U.S. National Phase under 35 U.S.C. § 371 of International Application PCT/US01/43244, filed Nov. 20, 2001, which claims the benefit of U.S. Provisional Application No. 60/252,942, filed Nov. 24, 2000, which is incorporated by reference herein.

FIELD

This patent specification relates to ultrasound-assisted surgery. More particularly, this patent specification relates to an apparatus and related methods for ultrasound-assisted surgical removal of tumors or other biological objects from a patient.

BACKGROUND

Breast cancer is the most common cancer among women other than skin cancer, and is the second leading cause of cancer death in women after lung cancer. The American Cancer Society currently estimates that there are about 182,800 new cases of invasive breast cancer per year among women in the United States and 40,800 deaths per year from the disease. Prevention and early diagnosis of breast cancer are of foremost importance. Because early breast cancer does not produce symptoms, the American Cancer Society recommends a mammogram and a clinical breast examination every year for women over the age of 40.

Although not a desirable procedure, the invasive surgical extraction of palpable tumors or suspicious lesions (hereinafter "tumors") becomes a necessity if a determination is made that a patient's tumor is potentially cancerous. During the surgery operation, it is highly desirable to remove the entire tumor from the patient, and not leave any part of it behind inside the patient. Accordingly, a section of tissue that the surgeon believes to completely surround the tumor is removed from the patient and then sent to a laboratory for further analysis. As used herein, the term "specimen" denotes the section of tissue removed by the surgeon, the term "tumor" refers to the actual tumor itself, and the term "surrounding tissue" refers to the portion of the specimen that surrounds the tumor.

Currently, there is a problem with prior art surgery techniques in tumor extraction. Because many tumors contain abnormal shapes such as small protruding spiculations, it sometimes happens that the surgeon does not capture a large enough specimen, causing some of the tumor to remain inside the patient. Unfortunately, the fact that the tumor was not completely removed is discovered later in the laboratory, well after the surgery has taken place and the patient is closed up. This is unfortunate for the patient because the cancer can spread further in the meantime. Also, a second painful and expensive extraction surgery will be required.

Accordingly, it would be desirable to provide a method and system for allowing a surgeon to be immediately aware of whether the surrounding tissue of a specimen completely surrounds the tumor, prior to the time that the patient is closed up.

SUMMARY

A method and system for ultrasound-assisted surgical removal of a tumor or other biological object from a patient, the tumor requiring complete removal such that no portion thereof remains inside the patient, is provided. According to a preferred embodiment, a specimen containing the tumor is extracted from the patient and suspended in a container holding an acoustically conductive fluid. An ultrasound probe is brought into acoustic communication with the fluid and scans the specimen, preferably at an acoustic power setting higher than a maximum ultrasonic power permitted on live human tissue. Resulting two-dimensional and/or three-dimensional ultrasound images of the specimen, which have a higher quality due to the increased acoustic power of the scan, are viewed on an output display for examining whether any portion of the tumor comes into contact with a surface of the specimen. Preferably, the ultrasound images are segmented and processed by the ultrasound system in a manner that further assists in the determination of whether the specimen contains the entire tumor.

DETAILED DESCRIPTION

Figure 1:
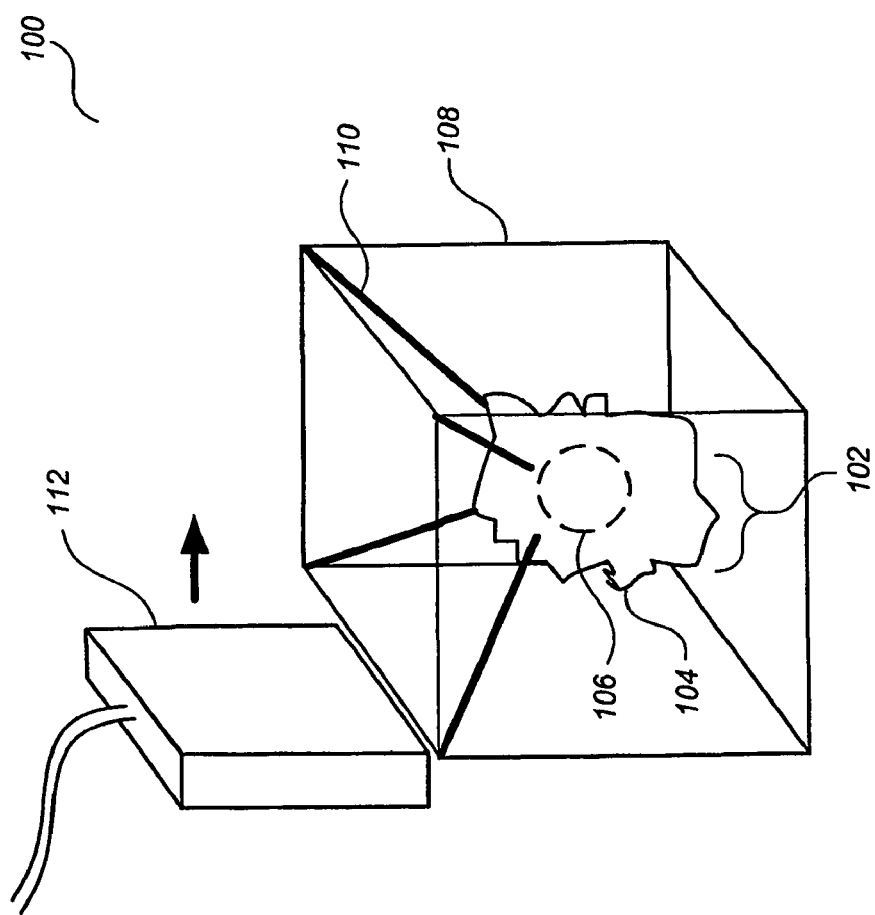
FIG. 1 illustrates an apparatus for ultrasonically scanning a specimen in accordance with a preferred embodiment.

FIG. 1 shows a conceptual diagram of a configuration 100 for using an ultrasound imaging system to assist the surgeon in instantly determining whether the surface of an extracted specimen completely surrounds the tumor. According to a preferred embodiment, immediately upon removal of a specimen 102 from the patient, the surgeon or an attending medical staff member suspends the specimen 102 in a container 108. The specimen 102 comprises a tumor portion 106 and surrounding tissue portion 104. The specimen 102 is suspended in the container 108 using a plurality of suspending devices 110, which can comprise surgical string and surgical clamps or hooks to grab the specimen and suspend it. The surgical string, clamps, hooks, etc. used to suspend the specimen 102 should be composed of ultrasonically transparent materials. The container 108 must be filled with a fluid such as water or gel surrounding the specimen 102. As an alternative to mechanically hanging the specimen in the container 108, a liquid or gel having a specific gravity similar to that of the specimen can be used, such that the specimen is automatically suspended in the container 108 without mechanical assistance.

An ultrasound transducer 112 is then moved across the surface of the container 108 as needed to generate a plurality of ultrasound slices. The ultrasound transducer 112 is mechanically coupled to a computer-controlled servo-motor or spring-based system, which automatically moves the transducer in a predetermined path and precisely monitors the transducer position corresponding to each ultrasound slice. Alternatively, a position sensing system, such as the miniBIRD 800™ position sensing system available from Ascension Technology Corp. of Burlington, Vt., may be used during this process to automatically detect the position and orientation of the ultrasound transducer for each slice.

According to a preferred embodiment, the ultrasound transducer 112 is of very high power as compared to conventional medical ultrasound systems. Because the specimen is not inside the patient, government regulations (such as Food and Drug Administration regulations in the United States) limiting the power of ultrasound transducers do not apply. Because of the use of a high power transducer, the ultrasound slices are high-quality, high-resolution images having high signal-to-noise ratios as compared to conventional medical ultrasound slices.

The ultrasound slices are then processed to segment the tumor 106 from the surrounding tissue 104 and generate a volumetric representation of the specimen 102. This processing may be performed in accordance with methods described in Cheng, X. Y.; Akiyama, I.; Itoh, K.; Wang, Y.; Taniguchi, N.; Nakajima, M., "Automated Detection of Breast Tumors in Ultrasonic Images Using Fuzzy Reasoning," *Proceedings of the International Conference on Image Processing, Volume III*, pp. 420–423, IEEE Computer Society (Oct. 26–29, 1997), and Cheng, Xiangyong, *A Study on Automated Extraction of Breast Tumors Using Three Dimensional Ultrasonic Echography*, Ph.D. Thesis, Keio University, Japan (1997), which are incorporated by reference herein.

Figure 2:
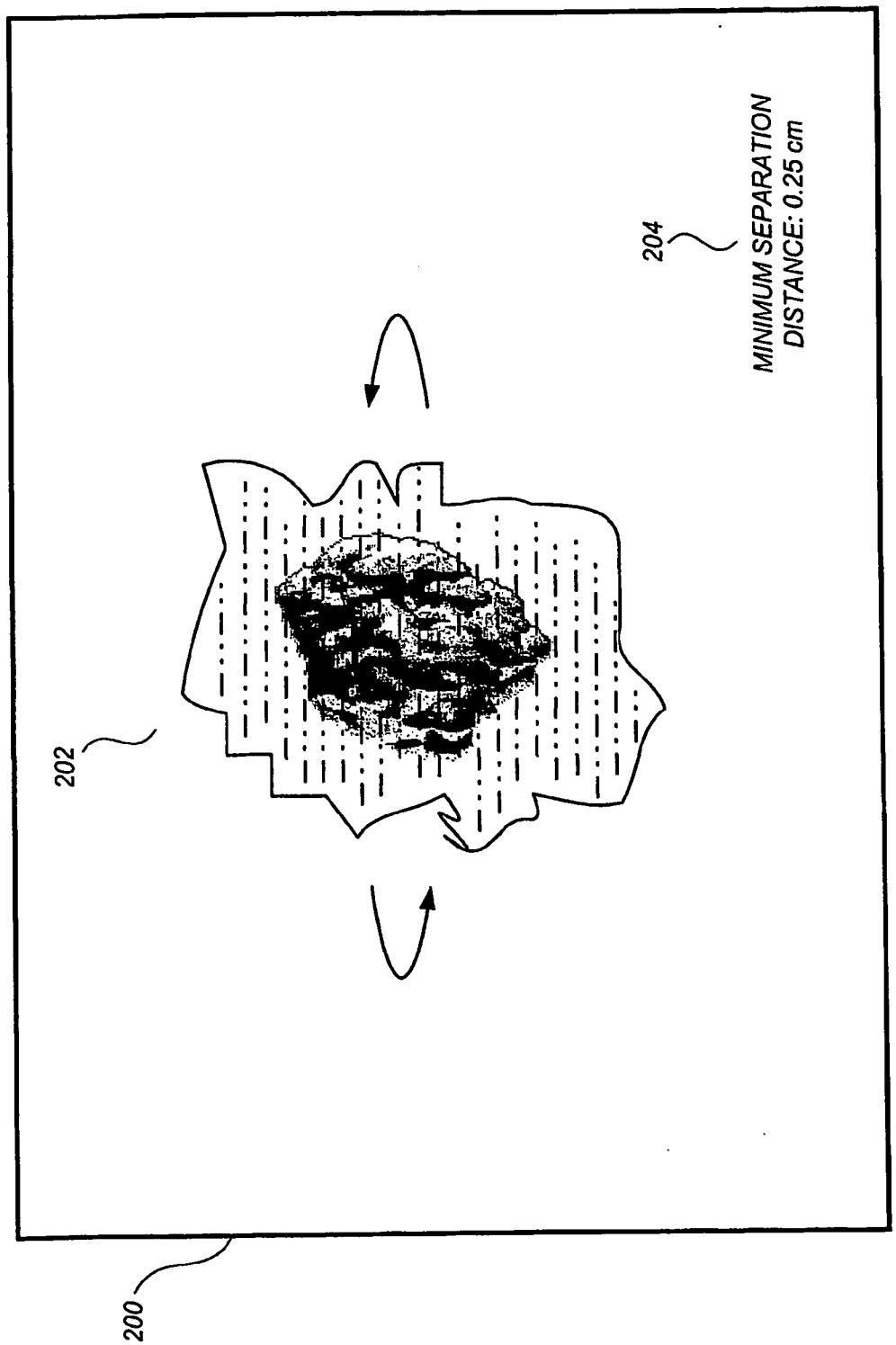
FIG. 2 illustrates an ultrasound display in accordance with a preferred embodiment.

FIG. 2 shows an ultrasound display 200 showing a three dimensional volumetric representation 202 of the specimen 102 in accordance with a preferred embodiment. The volumetric representation 202 comprises a semitransparent surface denoting the surface of the surrounding tissue 106 as it surrounds a three-dimensional representation of the tumor 104. Preferably, the volumetric representation 202 is rotated around an axis at a user-adjustable rotation speed for complete viewing. It has been found that the volumetric representation 202 can provide a very useful method for the surgeon to visually determine whether or not the tumor portion 106 protrudes beyond the surface of the surrounding tissue portion 104.

In another preferred embodiment, again using methods known in the art, an ultrasound processing system can process the above volumetric representation and compute a minimum separation distance between the tumor 106 and the surface of the surrounding tissue portion 104, which may then be displayed to the physician concurrently with the rotating volumetric representation 202, as shown by element 204 in FIG. 2. Alternatively, or in addition to the three dimensional volumetric representation, two dimensional slices of the specimen may be shown to the physician in sequence, who may then determine the closest distance between the tumor and surrounding specimen tissue on a per slice basis.

Thus, the method and system of the preferred embodiments can significantly enhance breast cancer patient care by allowing instant specimen diagnosis for verifying that the entire tumor was removed, thereby reducing the possibility of further spreading of the cancer and the pain of a second extraction surgery. It is to be appreciated that the method and system of the preferred embodiments is not necessarily limited to breast cancer applications, but can be used in a variety of surgical applications where instantaneous specimen analysis is required.

Figure 3:
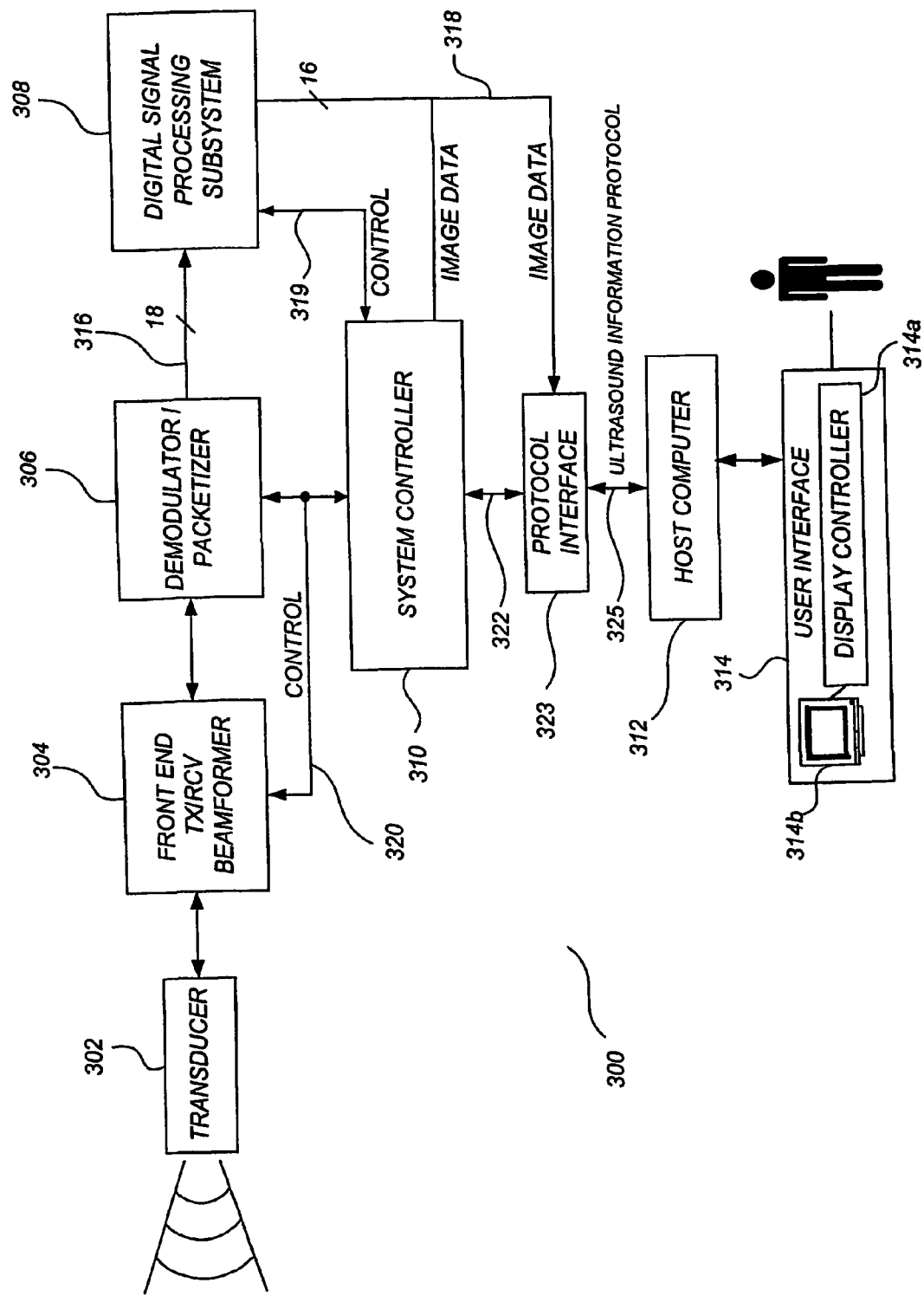
FIG. 3 illustrates a block diagram of an ultrasound system in accordance with a preferred embodiment.

FIG. 3 shows a diagram of an ultrasound system 300 that may be used in accordance with a preferred embodiment. The ultrasound system 300 is similar to a system described in commonly assigned Ser. No. 09/449,095, filed Nov. 24, 1999, and hereby incorporated by reference herein, although any of a variety of other ultrasound system architectures may be used. Ultrasound system 300 comprises a transducer 302, a front end transmit/receive beamformer 304, a demodulator/packetizer 306, a digital signal processing subsystem 308, a system controller 310, a host computer 312, and a user interface 314, the user interface 314 including a display controller 314a and a display 314b. Using known methods, transducer 302 comprises an array of transducer elements that generates focused acoustic signals responsive to signals generated by front end transmit/receive beamformer 304. Also using known methods, transducer 302 generates electrical signals responsive to received echoes that are processed by front end transmit/receive beamformer 304, which in turn transmits digital RF samples to demodulator/packetizer 306 for further processing.

Demodulator/packetizer 306 comprises demodulating circuitry that receives the digital RF samples from front end transmit/receive beamformer 304 and generates digital samples using known methods. Demodulator/packetizer 306 further comprises packetizing circuitry that generates ultrasound information packets from the digital samples, and transmits the ultrasound information packets to digital signal processing subsystem 308 over a bus 316. Processed image data from digital processing subsystem 308 is provided to a protocol interface 323 over an output bus 318. High-speed serial bus 325 transfers information to a host computer 312. Among other functions, host computer 312 also comprises a scan converter for converting image data samples, which generally correspond to digital samples from non-rectangular grids, into pixelized format for display on a computer monitor. Host computer 312 is coupled to user interface 314, the user interface 314 comprising a display controller 314a and display 314b. The display controller 314a processes information for display such that outputs described and shown herein are provided to the display 314b. The user interface also receives user commands that manipulate the displayed images and/or other aspects of the ultrasound system 300.

When used in a preferred embodiment disclosed in this patent specification, ultrasound probe 302 is used as probe 112 but is driven at a higher level of ultrasound power, e.g., at a level higher than suitable for human patients. Alternatively, a special, high-power probe 112 is connected in place of probe 302. In either case, the equipment of FIG. 3 is adjusted or modified as needed to drive the ultrasound probe at the requisite high power.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments are not intended to limit their scope, which is limited only by the scope of the claims set forth below.

What is claimed is:

1. An apparatus for facilitating examination of a specimen removed from a patient during a surgical removal process, the specimen containing a tumor and surrounding tissue, comprising:

a container structured to suspend the specimen in an acoustically conductive fluid such that the acoustically conductive fluid substantially surrounds the specimen;

an ultrasound probe for placement in acoustic communication with the acoustically conductive fluid, the ultrasound probe having an ultrasonic power setting higher than a maximum ultrasonic power permitted on live human tissue;

an ultrasound processor coupled to the ultrasound probe, the ultrasound processor receiving scan information from the ultrasound probe and computing ultrasound images of the specimen therefrom; and a display device coupled to the ultrasound processor for displaying the ultrasound images of the specimen to a user, said high ultrasonic power setting resulting in ultrasound images having higher signal-to-noise characteristics as compared to images obtained from probes set below said maximum ultrasonic power, said high signal-to-noise ultrasound images enhancing the user's ability to determine whether or not the tumor is completely surrounded by the surrounding tissue in the specimen.

2. The apparatus of claim 1, wherein the ultrasound images displayed to the user are two-dimensional ultrasound slices.

3. The apparatus of claim 1, further comprising a position determining system coupled to said ultrasound probe and to said ultrasound processor, said position determining system structured to detect positions of the ultrasound probe as it scans the specimen and to provide said positions to the ultrasound processor, said ultrasound processor computing a volumetric representation of the specimen, said display displaying a three-dimensional volumetric representation of the specimen.

4. The apparatus of claim 3, further comprising a user input for receiving image manipulation commands from the user, the three-dimensional volumetric representation being rotated and/or scaled on the display device according to said image manipulation commands.

5. The apparatus of claim 3, said ultrasound processor segmenting the tumor and the surrounding tissue, wherein said three-dimensional volumetric representation displayed to the user comprises segmented versions of the tumor and surrounding tissue.

6. The apparatus of claim 5, said ultrasound processor computing a closest distance between a tumor surface and a specimen surface, said display device displaying said closest distance in numerical form.

7. The apparatus of claim 1, wherein the specimen is suspended in the container by ultrasonically transparent mechanical supports extending from a frame of the container.

8. The apparatus of claim 1, wherein the acoustically conductive fluid is a gel having a specific gravity similar to that of the specimen, the specimen being supported solely by the gel.

9. An apparatus for facilitating examination of a specimen removed from a patient during a surgical removal process, the specimen containing a tumor and surrounding tissue, comprising:

a container structured to suspend the specimen in an acoustically conductive fluid such that the acoustically conductive fluid substantially surrounds the specimen;

an ultrasound probe for placement in acoustic communication with the acoustically conductive fluid to scan the specimen;

a position determining system coupled to said ultrasound probe to detect positions of the ultrasound probe as it scans the specimen;

an ultrasound processor coupled to the ultrasound probe and to the position determining system, the ultrasound processor receiving scan information from the ultrasound probe and corresponding probe positions from the position determining system, the ultrasound processor computing a volumetric representation of the specimen; and a display device coupled to the ultrasound processor for displaying the volumetric representation of the specimen to a user, the volumetric representation of the specimen enhancing the user's ability to determine whether or not the tumor is completely surrounded by the surrounding tissue in the specimen.

10. The apparatus of claim 9, further comprising a user input for receiving image manipulation commands from the user, the volumetric representation being rotated and/or scaled on the display device according to said image manipulation commands.

11. The apparatus of claim 9, said ultrasound processor segmenting the tumor and the surrounding tissue, wherein said volumetric representation displayed to the user comprises segmented versions of the tumor and surrounding tissue.

12. The apparatus of claim 11, said ultrasound processor computing a closest distance between a tumor surface and a specimen surface, said display device displaying said closest distance in numerical form.

13. The apparatus of claim 12, wherein said ultrasound probe has an ultrasonic power setting higher than a maximum ultrasonic power permitted on live human tissue, said high ultrasonic power setting resulting in ultrasound images having improved signal-to-noise characteristics as compared to in vivo ultrasound scans.

14. The apparatus of claim 9, wherein the acoustically conductive fluid is a gel having a specific gravity comparable to that of the specimen, and wherein the specimen is supported solely by the gel.

15. A surgical method of removing a biological object from a patient, the biological object requiring complete removal such that no portion thereof remains inside the patient, comprising:

surgically extracting a specimen from the patient, the specimen comprising the biological object and a surrounding tissue portion, the surrounding tissue portion substantially surrounding the biological object according to an initial approximation of a spatial extent of the biological object;

ultrasonically scanning the specimen using an acoustic power setting higher than a maximum ultrasonic power permitted on live human tissue;

viewing a display device displaying one or more ultrasound images of the specimen derived from the ultrasonic scan thereof;

determining whether the specimen completely contains the biological object by examining whether any portion of the biological object comes into contact with a surface of the specimen according to said ultrasound images; and concluding the removal procedure for the biological object if no portion thereof comes into contact with the surface of the specimen.

16. The surgical method of claim 15, ultrasonically scanning the extracted specimen comprising:

suspending the specimen in an acoustically conductive fluid such that the acoustically conductive fluid surrounds the specimen; and bringing an ultrasound probe into contact with the acoustically conductive fluid such that an acoustic coupling is formed between the specimen and the ultrasound probe.

17. The surgical method of claim 15, wherein said biological object is a breast tumor.

18. The surgical method of claim 15, wherein said one or more ultrasound images are three-dimensional volumetric representations of the specimen.

19. The surgical method of claim 18, further comprising manipulating an ultrasound system user input to cause said three-dimensional volumetric representation to be rotated and/or scaled on the display device.

20. The surgical method of claim 19, further comprising viewing a numerical metric on the display device, the numerical metric corresponding to a closest distance between the biological object and the specimen surface as computed by an ultrasound processor processing the ultrasound images.

21. An apparatus for facilitating examination of a specimen removed from a patient during a surgical removal process, the specimen containing a tumor and surrounding tissue, comprising:

means for suspending the specimen in an acoustically conductive fluid such that the acoustically conductive fluid substantially surrounds the specimen;

means for examining the suspended specimen with ultrasound at an ultrasonic power higher than a maximum ultrasonic power permitted on live human tissue;

means for processing ultrasound information received from the means for examining and for computing ultrasound images of the specimen therefrom; and means for displaying the ultrasound images of the specimen to a user, said high ultrasonic power resulting in ultrasound images having higher signal-to-noise characteristics as compared to images obtained using ultrasound power below said maximum ultrasonic power, said high signal-to-noise ultrasound images enhancing the user's ability to determine whether or not the tumor is completely surrounded by the surrounding tissue in the specimen.

* * * * *